United States Patent [19]

Wada et al.

[11] 4,180,678

[45] Dec. 25, 1979

[54] PROCESS FOR PREPARING METHACRYLIC ACID

[75] Inventors: Masahiro Wada; Michio Ueshima, both of Nishinomiya; Isao Yanagisawa, Ikeda; Michikazu Ninomiya, Kobe, all of Japan

[73] Assignee: Nippon Shokubai Kagaku Kogyo Co. Ltd., Osaka, Japan

[21] Appl. No.: 536,864

[22] Filed: Dec. 27, 1974

[30] Foreign Application Priority Data

Dec. 29, 1973 [JP] Japan .................................. 48-3630

[51] Int. Cl.² ...................... C07C 51/32; C07C 57/04
[52] U.S. Cl. .................................. 562/534; 252/435; 252/437; 252/467; 562/535
[58] Field of Search ................... 260/530 N; 252/435, 252/437; 562/534, 535

[56] References Cited

U.S. PATENT DOCUMENTS

| | | | |
|---|---|---|---|
| 3,795,703 | 3/1974 | Niina et al. | 260/530 N |
| 3,875,220 | 4/1975 | White et al. | 260/530 N |
| 4,075,244 | 2/1978 | Akiyama et al. | 562/535 |

Primary Examiner—Vivian Garner
Attorney, Agent, or Firm—Sherman & Shalloway

[57] ABSTRACT

A process for preparing methacrylic acid which comprises carrying out the catalytic vapor phase oxidation of methacrolein with a member selected from the group consisting of air and a molecular oxygen-containing gas in the presence of a novel catalytic oxide composition of the general formula $$Y_a X_b P_c Mo_d V_e O_f$$

Wherein Y is at least one metallic element selected from the group consisting of copper, cobalt, zirconium, bismuth, antimony and arsenic, X is at least one alkali metal element selected from the group consisting of sodium, potassium, rubidium and cesium, and a, b, c, d, e and f represent the atomic ratios of the several elements; and when d is 12, a is 0–10 and b is 0–10, c is 0.1–10, e is 0.1–10, and f is a value that is determined by the valences and atomic ratios of the several elements, with the proviso that the sum of a plus b is greater than zero.

8 Claims, No Drawings

PROCESS FOR PREPARING METHACRYLIC ACID

This invention relates to a process for preparing methacrylic acid by effecting the catalytic vapor phase oxidation of methacrolein by passing methacrolein over a catalyst along with either air or a molecular oxygen-containing gas.

A great number of catalyst compositions for preparing methacrylic acid by the catalytic vapor phase oxidation of methacrolein have been suggested to date. For example, with respect to the catalyst system consisting predominantly of P and Mo, there is disclosed in U.S. Pat. No. 3,761,516 a composition supported on carrier, consisting of P, Mo and As or a composition of the same components further incorporated with Al, while in German Laid Open Application No. 2,258,547 there is disclosed a catalyst composition consisting of P and Mo in which has been incorporated Tl and/or Rb and/or Cs and/or K, and further Cr and/or Si and/or Al and/or Ti. On the other hand, with respect to the catalyst system consisting predominantly of Mo and V, a Mc-V composition supported on silicon carbide is disclosed in German Laid Open Application No. 2,164,905, while a Mo-V-Sb composition supported on aluminum is disclosed in German Laid Open Application No. 2,038,763. On the other hand, in French Patent No. 2,040,546 there is disclosed a Mo-V-P catalyst.

However, when these suggested catalysts were tested further under actual operating conditions, only low yields could be obtained. Again, since the method of their use cannot be said to be effective, they cannot be considered to be fully satisfactory for commercial purposes. A particular shortcoming is that the amount of by-products formed by the use of these catalysts is great. Simultaneous reactions such as polymerization or decomposition over the catalyst or on the inside wall of the reactor are observed. Thus, when considered from the standpoint of commercial operations, such economic disadvantages as a reduction in catalyst life and contamination of the reaction apparatus as well as an increase in pressure loss are believed to be inevitable.

The object of the present invention is to provide a commercially advantageous process for preparing methacrylic acid by finding a new catalyst system that can overcome the shortcomings of these conventional catalysts.

We found that methacrylic acid could be prepared from methacrolein at a relatively low reaction temperature and moreover at a high selectivity when a catalytic oxide consisting of molybdenum, vanadium and phosphorus, along with at least one metal (Y) selected from the group consisting of copper, cobalt, zirconium, bismuth, antimony and arsenic, and/or at least one alkali metal (X), in specific proportions, was used. In addition, it was found that simultaneous reactions such as polymerization or decomposition over the catalyst or on the inside wall of the reactor during the reaction could be prevented.

Thus, there is provided according to this invention a process for preparing methacrylic acid which comprises carrying out the catalytic vapor phase oxidation of methacrolein with either air or a molecular oxygen-containing gas in the presence of a catalytic oxide represented by the general formula $$Y_a X_b P_c Mo_d V_e O_f$$

wherein Y is at least one metallic element selected from the group consisting of copper, cobalt, zirconium, bismuth, antimony and arsenic, X is at least one alkali metal element selected from the group consisting of sodium, potassium, rubidium and cesium, and a, b, c, d, e and f represent the atomic ratios of the several elements; and when d is 12, a is 0–10, preferably 0–8.0, b is 0–10, preferably 0–3.0, c is 0.1–10, preferably 0.5–5.0, e is 0.1–10, preferably 0.5–5.0, and f is a value that is determined by the valences and atomic ratios of the several elements, with the proviso that the sum of a plus b is greater than zero.

In this invention the foregoing catalytic oxide can be used as such, but it is also possible to use it supported on a carrier. As the carrier material, any of the usually used inert porous substances or those inert substances that can be granulated into a porous material will do. For example, such substances as alumina, silicon carbide, pumice stone, silica, zirconia, titanium oxides and magnesium silicate can be used either alone or as mixtures of two or more thereof.

Further, the catalyst of the invention process can not only be used with the fixed bed type reaction but also with the fluidized bed type reaction.

By way of example, a desirable procedure for preparing the invention catalyst will be described below. First of all, a complex is prepared by reacting vanadium pentoxide and orthophosphoric acid. Separately, an aqueous ammonium molybdate solution is added with orthophosphoric acid and, if necessary, a nitrate of either copper, cobalt, zirconium or bismuth, arsenous acid or antimony trioxide and completely reacted by heating to obtain a solution, to which the foregoing complex is added, followed, if necessary, by the addition of an aqueous solution of either a hydroxide, sulfate or nitrate of an alkali metal to obtain a combined solution, which solution is used as such or after making it into a molded or supported catalyst. In preparing the molded catalyst, a powdery carrier material is admixed with the foregoing combined solution, after which the mixture is concentrated or evaporated to dryness and the concentrate or dried product is molded, and then calcined at a temperature of 300°–600° C. under circulation of air, thus preparing a molded catalyst. On the other hand, if the foregoing combined solution is deposited on a carrier material and calcined in like manner, a supported catalyst is prepared. Further, it is also possible to use aqueous solutions of vanadates such as vanadyl oxalate, vanadyl sulfate, etc., instead of the foregoing complex in preparing the aforesaid combined solution. Again, the starting catalyst substance is not limited to the aforementioned compounds, it being possible to use such other compounds as inorganic and organic acid salts and metallic acid salts that are capable of being decomposed by calcination.

In accordance with a preferred embodiment of the present invention, methacrylic acid is prepared advantageously by introducing a starting gas consisting of 1–10 volume % of methacrolein, 1–15 volume % of oxygen, 5–60 volume % of steam and the balance consisting of an inert gas such as nitrogen, carbon dioxide, carbon monoxide, etc., over the aforementioned catalytic oxide at a temperature of 200°–400° C., preferably 230°–350° C. and a pressure of normal atmospheric pressure—10 atm. at a space velocity of 500–3000 hr$^{-1}$. Also conveniently usable in this invention as the starting gas is that containing predominantly methacrolein obtained by the catalytic vapor phase oxidation of isobutylene or tertiary butanol.

The characteristics of the present invention resulting from the use of such a catalytic oxide include, the formation of less by-products with the consequence that simultaneous reactions such as polymerization over the catalyst or on the inside wall of the reactor and decomposition are checked, and the results obtained are much more superior to those obtained in the case of the prior art in that the rate of reaction of methacrolein is 60–90 mol %, while the selectivity for methacrylic acid is 70–90 mol %.

The rate of reaction, selectivity and per-mass yield, as used herein, are defined as follows:

Rate of reaction (%) =
$\frac{\text{Number of mols of methacrolein reacted}}{\text{Number of mols of methacrolein fed}} \times 100$ Selectivity (%) =
$\frac{\text{Number of mols of methacrylic acid formed}}{\text{Number of mols of methacrolein reacted}} \times 100$ Per-pass yield (%) =
$\frac{\text{Number of mols of methacrylic acid formed}}{\text{Number of mols of metacrolein fed}} \times 100$ The following non-limitative examples will be given for more specifically illustrating the invention.

EXAMPLE 1

106 grams of ammonium molybdate was dissolved in 400 ml of water. Separately, 5.8 grams of 85% orthophosphoric acid was diluted with 30 ml of water, in which 3.6 grams of copper nitrate was dissolved. This latter aqueous solution was added to the foregoing aqueous ammonium molybdate solution, after which the combined solution was aged by heating it with thorough stirring. Further, separately, 5.8 grams of 85% orthophosphoric acid was diluted with 30 ml of water, to which was then added 4.6 grams of vanadium pentoxide followed by evaporating the water from the mixture by heating it with stirring to obtain a yellow complex. This complex was then added to the foregoing reaction precipitate of phosphorus, molybdenum and copper, after which finally a solution of 2.8 grams of potassium hydroxide in 30 ml of water was added followed by concentration to dryness. The resulting solid was then dried for a further 4 hours at 200° C., comminuted into particles of about 5-mm size, and thereafter calcined for 5 hours at 400° C. under circulation of air. The composition of the so obtained catalyst, when expressed as atomic ratios of their metallic elements exclusive of oxygen, was $P_2Cu_{0.3}K_1V_1Mo_{12}$.

Fifty cc. of this catalyst was packed in a stainless steel U-shaped reaction tube having an inside diameter of 25 mm, and the packed tube was immersed in a molten salt of 280° C. (NT 280° C.). A gaseous mixture composed of 4 vol. % of methacrolein, 10 vol. % of oxygen, 44 vol. % of nitrogen and 40 vol. % of steam was introduced into the foregoing reaction tube and, while maintaining the space velocity of the gaseous mixture at 1000 hr$^{-1}$, the oxidation reaction of methacrolein was carried out with the results shown in Table 1.

EXAMPLE 2

The oxidation reaction was carried out under indentical conditions as in Example 1 using the same catalyst as that obtained therein but in NT 260° C. The results obtained are shown in Table 1.

EXAMPLES 3–5

The catalyst was prepared under identical conditions as in Example 1, except that instead of 3.6 grams of copper nitrate used therein 7.3 grams of cobalt nitrate (Example 3), 3.8 grams of arsenous acid (Example 4) or 5.7 grams of antimony trichloride (Example 5) was used. The so obtained catalyst was then used in carrying out the oxidation reaction of methacrolein with the results shown in Table 1.

EXAMPLE 6

The same catalyst as that obtained in Example 1 was used, and a gaseous mixture consisting of 5 mol % of methacrolein, 10 mol % of oxygen, 45 mol % of nitrogen and 40 mol % of steam was introduced under the reaction conditions shown in Table 1 to carry out the oxidation reaction of methacrolein. The results obtained are shown in Table 1.

EXAMPLE 7

The same catalyst as that obtained in Example 4 was used, and the oxidation reaction of methacrolein was carried out by introducing a gaseous mixture consisting of 5 mol % of methacrolein, 10 mol % of oxygen, 45 mol % of nitrogen and 40 mol % of steam under the conditions indicated in Table 1 with the results shown therein.

EXAMPLES 8–9

The preparation of the of catalysts was carried out under identical conditions as in Example 1 but using instead of 3.6 grams of copper nitrate 12.0 grams of bismuth nitrate (Example 8) or 8.9 grams of zirconium sulfate (Example 9). The so obtaind catalysts were used, and the oxidation reaction of methacrolein was then carried out by operating as in Example 1. The results obtained are shown in Table 1.

EXAMPLES 10–12

Catalysts having the compositions shown in Table 1 were prepared by following the procedure described in Example 1 but instead of using 2.8 grams of potassium hydroxide as used therein 4.2 grams of sodium nitrate (Example 10), 6.7 grams of rubidium sulfate (Example 11) or 9.7 grams of cesium nitrate (Example 12) was used. The so obtained catalysts were then used in carrying out the oxidation reaction of methacrolein as in Example 1, with the results shown in Table 1.

EXAMPLE 13

A catalyst having the composition shown in Table 1 was prepared by repeating Example 1 but without adding the potassium nitrate used therein. This catalyst was used, and the oxidation reaction of methacrolein was carried out under identical conditions as in Example 1. The results obtained are shown in Table 1.

EXAMPLE 14

A catalyst having the composition shown in Table 1 was prepared by operating as in Example 1, except that in the step of preparing the complex of orthophosphoric acid and vanadium pentoxide 2.9 grams of 85% orthophosphoric acid and 4.6 grams of vanadium pentoxide were used. The so obtained catalyst was used, and the oxidation reaction of methacrolein was carried out under identical conditions as in Example 1. The results obtained are shown in Table 1.

EXAMPLE 15

A catalyst was prepared by operating as in Example 1, except that in the step of preparing the complex of orthophosphoric acid and vanadium pentoxide 11.6 grams of 85% orthophosphoric acid and 4.6 grams of vanadium pentoxide were used. The so obtained catalyst was then used, and the oxidation reaction of methacrolein was carried out under identical conditions as in Example 1. The results obtained are shown in Table 1.

EXAMPLE 16

106 grams of ammonium molybdate was dissolved in 400 ml of water. Separately, 11.6 grams of 85% orthophosphoric acid was diluted with 30 ml of water, in which 3.6 grams of copper nitrate was then dissolved. This latter aqueous solution was added to the foregoing aqueous ammonium molybdate solution, after which the combined solution was aged by heating it with thorough stirring. Further, separately, 11.6 grams of 85% orthophosphoric acid was diluted with 30 ml of water, to which was then added 6.9 grams of vanadium pentoxide followed by evaporating the water from the mixture by heating it with stirring to obtain a yellow complex. This complex was then added to the foregoing reaction precipitate of phosphorus, molybdenum and copper, after which finally a solution of 2.8 grams of potassium hydroxide in 30 ml of water was added. Thereafter, the experiment was operated as in Example 1 to obtain a catalyst having the composition shown in Table 1. The so obtained catalyst was then used, and the oxidation reaction of methacrolein was carried out under identical conditions as in Example 1. The results obtained are shown in Table 1.

EXAMPLE 17

A catalyst having the composition shown in Table 1 was prepared by operating as in Example 1, except that in the step or preparing the complex of orthophosphoric acid and vanadium pentoxide 5.8 grams of 85% orthophosphoric acid and 9.2 grams of vanadium pentoxide were used. The so obtained catalyst was then used, and the oxidation reaction of methacrolein was carried out under identical conditions as in Example 1 with the results shown in Table 1.

EXAMPLE 18

A catalyst having the composition shown in Table 1 was prepared by operating as in Example 1, except that in the step of preparing the complex of orthophosphoric acid and vanadium pentoxide 5.8 grams of 85% orthophosphoric acid and 13.8 grams of vanadium pentoxide were used. Using the so obtained catalyst, the oxidation reaction of methacrolein was then carried out under identical conditions as in Example 1. The results obtained are shown in Table 1.

EXAMPLES 19–20

Catalysts were prepared as in Example 3 but varying the amount used of the cobalt nitrate [14.6 grams (Example 19) or 29.2 grams (Example 20)] to obtain catalysts having the compositions shown in Table 1. The so obtained catalysts were used, and the oxidation reaction of methacrolein was carried out under identical conditions as in Example 1. The results obtained are shown in Table 1.

EXAMPLES 21–22

Catalysts having the compositions shown in Table 1 were prepared by operating as in Example 3 but varying the amount used of the potassium hydroxide in preparing the catalyst [4.2 grams (Example 21) or 5.6 grams (Example 22)]. The so obtained catalysts were then used, and the oxidation reaction of methacrolein was carried out under identical conditions as in Example 1. The results obtained are shown in Table 1.

EXAMPLE 23

106 grams of ammonium molybdate was dissolved in 400 ml of water. Separately, 5.8 grams of 85% orthophosphoric acid was diluted with 30 ml of water, in which was then dissolved 3.6 grams of copper nitrate. This latter solution was added to the foregoing aqueous ammonium molybdate solution, after which the combined solution was aged by heating it with thorough stirring. Further, separately, 2.9 grams of 85% orthophosphoric acid was diluted with 30 ml of water, to which was then added 4.6 grams of vanadium pentoxide followed by evaporating the water from the mixture by heating it with stirring to obtain a yellow complex. This complex was then added to the foregoing reaction precipitate of phosphorus, molybdenum and copper followed by the further addition of 14.5 grams of antimony trioxide as such and finally a solution of 2.8 grams of potassium hydroxide in 30 ml of water, after which the mixture was concentrated to dryness. Thereafter, the experiment was operated as in Example 1 to obtain a catalyst having the composition shown in Table 1. This catalyst was used, and the oxidation reaction of methacrolein was carried out as in Example 1 with the results shown in Table 1.

EXAMPLE 24

A catalyst was prepared under identical conditions as in Example 23 but using 29.0 grams of antimony trioxide. The so obtained catalyst was used, and the oxidation reaction of methacrolein was carried out by operating as in Example 1. The results obtained are shown in Table 1.

EXAMPLE 25

A catalyst was prepared by operating as in Example 24 but using instead of the aqueous potassium hydroxide solution a solution of 2.8 grams of potassium hydroxide and 4.9 grams of cesium nitrate in 30 ml of water. This catalyst was used and methacrolein was oxidized as in Example 1 with the results shown in Table 1.

EXAMPLE 26

A catalyst was prepared by operating as in Example 23 but using 1.9 grams of cobalt oxide instead of antimony trioxide. The so obtained catalyst was used and methacrolein was oxidized as in Example 1 with the results shown in Table 1.

Table 1

| Example No. | Catalyst Composition (Atomic ratios of elements other than oxygen) | | | | | | | Reaction Conditions | | Conversion of methacrolein (mol %) | Selectivity for methacrylic acid (mol %) | Per-pass Yield of methacrylic acid (mol %) |
|---|---|---|---|---|---|---|---|---|---|---|---|---|
| | Y | | X | | P | V | Mo | Space velocity (hr$^{-1}$) | NT (°C.) | | | |
| 1  | Cu | 0.3 | K  | 1.0 | 2.0 | 1.0 | 12 | 1000 | 280 | 90.0 | 78.0 | 70.2 |
| 2  | Cu | 0.3 | K  | 1.0 | 2.0 | 1.0 | 12 | 1000 | 260 | 62.3 | 87.3 | 54.3 |
| 3  | Co | 0.5 | K  | 1.0 | 2.0 | 1.0 | 12 | 1000 | 300 | 80.0 | 77.5 | 62.0 |
| 4  | As | 0.5 | K  | 1.0 | 2.0 | 1.0 | 12 | 1000 | 305 | 85.0 | 77.0 | 65.5 |
| 5  | Sb | 0.5 | K  | 1.0 | 2.0 | 1.0 | 12 | 1000 | 320 | 85.0 | 78.9 | 63.5 |
| 6  | Cu | 0.3 | K  | 1.0 | 2.0 | 1.0 | 12 | 2000 | 295 | 84.3 | 79.5 | 67.0 |
| 7  | As | 0.5 | K  | 1.0 | 2.0 | 1.0 | 12 | 2000 | 320 | 78.0 | 82.3 | 64.2 |
| 8  | Bi | 0.5 | K  | 0.7 | 2.0 | 1.0 | 12 | 1000 | 310 | 88.5 | 70.1 | 62.0 |
| 9  | Zr | 0.5 | K  | 0.5 | 2.0 | 1.0 | 12 | 1000 | 280 | 78.5 | 75.0 | 58.9 |
| 10 | Cu | 0.3 | Na | 1.0 | 2.0 | 1.0 | 12 | 1000 | 290 | 72.5 | 75.9 | 55.0 |
| 11 | Cu | 0.3 | Rb | 1.0 | 2.0 | 1.0 | 12 | 1000 | 292 | 76.0 | 71.7 | 54.5 |
| 12 | Cu | 0.3 | Cs | 1.0 | 2.0 | 1.0 | 12 | 1000 | 300 | 76.5 | 74.9 | 57.3 |
| 13 | Cu | 0.3 | —  | 0   | 2.0 | 1.0 | 12 | 1000 | 295 | 69.2 | 74.0 | 51.3 |
| 14 | Cu | 0.3 | K  | 1.0 | 1.5 | 1.0 | 12 | 1000 | 280 | 85.6 | 75.4 | 64.5 |
| 15 | Cu | 0.3 | K  | 1.0 | 3.0 | 1.0 | 12 | 1000 | 305 | 30.7 | 75.6 | 61.0 |
| 16 | Cu | 0.3 | K  | 1.0 | 4.0 | 1.5 | 12 | 1000 | 320 | 75.8 | 73.0 | 55.3 |
| 17 | As | 0.5 | K  | 1.0 | 2.0 | 2.0 | 12 | 1000 | 310 | 80.0 | 73.2 | 58.6 |
| 18 | Cu | 0.3 | K  | 1.0 | 2.0 | 3.0 | 12 | 1000 | 320 | 72.6 | 77.1 | 56.0 |
| 19 | Co | 1.0 | K  | 1.0 | 2.0 | 1.0 | 12 | 1000 | 310 | 75.6 | 75.4 | 57.0 |
| 20 | Co | 2.0 | K  | 1.0 | 2.0 | 0.7 | 12 | 1000 | 300 | 78.5 | 70.2 | 55.1 |
| 21 | Co | 0.5 | K  | 1.5 | 2.0 | 0.7 | 12 | 1000 | 300 | 76.5 | 78.0 | 59.7 |
| 22 | Co | 0.5 | K  | 2.0 | 2.0 | 1.5 | 12 | 1000 | 305 | 70.3 | 78.6 | 55.2 |
| 23 | Cu Sb | 0.3 2.0 | K | 1.0 | 1.5 | 1 | 12 | 1000 | 266 | 89.6 | 73.7 | 66.1 |
| 24 | Cu Sb | 0.3 4.0 | K | 1.0 | 1.5 | 1 | 12 | 1000 | 275 | 92.4 | 74.3 | 68.7 |
| 25 | Cu Sb | 0.3 4.0 | K Cs | 1.0 0.5 | 1.5 | 1 | 12 | 1000 | 285 | 91.0 | 77.4 | 70.5 |
| 26 | Cu Co | 0.3 0.5 | K | 1.0 | 1.5 | 1 | 12 | 1000 | 260 | 88.3 | 72.2 | 63.8 |

EXAMPLE 27

106 grams of ammonium molybdate was dissolved in 200 ml of water, to which solution was then added 5.8 grams of 85% orthophosphoric acid, following which the mixture was well stirred with heating until a white precipitate was formed. Separately, 4.6 grams of vanadium pentoxide was added to a solution of 8.8 grams of oxalic acid in 100 ml of water with heating and well stirred until a deep blue homogeneous solution was obtained. This oxalic acid solution was then added to the foregoing precipitate-containing solution obtained from ammonium molybdate and orthophosphoric acid, after which a solution of 2.8 grams of potassium hydroxide in 30 ml of water was added, and the combined solution was concentrated to dryness. The resulting solid was dried for 4 hours at 200° C. followed by comminution and molding into cylindrical tablets 5 mm (diameter)×5 mm in size. The tablets were calcined for 4 hours at 400° C. The composition of the so obtained catalyst, when expressed in atomic ratios exclusive of oxygen, was $P_1Mo_{12}V_1K_1$. Fifty ml of this catalyst was packed in a stainless steel U-shaped tube, and the tube was immersed in a molten salt heated at 280° C. (NT 280° C.). This was followed by introducing into the reaction tube a gaseous mixture consisting of 4 vol. % of methacrolein, 10 vol. % of oxygen, 46 vol. % of nitrogen and 40 vol. % of steam and carrying out the reaction while maintaining the space velocity of the gaseous mixture at 1000 hr$^{-1}$. The results obtained are shown in Table 2. As products, there was noted the formation of acetic acid, carbon dioxide and carbon monoxide in addition to methacrylic acid.

EXAMPLE 28

A catalyst prepared as in Example 27 was used, and the reaction was carried out as described therein, except that the reaction tube was immersed in NT 260° C. The results obtained are shown in Table 2.

EXAMPLES 29–39

The catalysts shown in Table 2 were prepared in accordance with the method described in Example 27. The so prepared catalysts were used, and the reaction was carried out as in Example 27 in NT indicated in Table 2. The results obtained are shown in Table 2. There were however the following exceptions. Instead of the 2.8 grams of potassium hydroxide used in Example 27, in Examples 37, 38 and 39 4.3 grams of sodium nitrate, 6.7 grams of rubidium sulfate and 9.8 grams of cesium nitrate, respectively were used.

Table 2

| Example No. | Catalyst Composition (Atomic ratios of elements other than oxygen) | | | | | | | NT (°C.) | Conversion of methacrolein (mol %) | Selectivity for methacrylic acid (mol %) | Per-pass yield of methacrylic acid (mol %) |
|---|---|---|---|---|---|---|---|---|---|---|---|
| | P | V | Na | K | Rb | Cs | Mo | | | | |
| 27 | 1 | 1 | — | 1.0 | — | — | 12 | 280 | 82.5 | 75.2 | 62.0 |
| 28 | 1 | 1 | — | 1.0 | — | — | 12 | 260 | 63.6 | 86.5 | 55.0 |
| 29 | 1 | 1 | — | 0.5 | — | — | 12 | 310 | 79.9 | 72.0 | 57.5 |
| 30 | 1 | 1 | — | 1.5 | — | — | 12 | 310 | 70.5 | 73.0 | 51.5 |
| 31 | 1 | 1 | — | 2.0 | — | — | 12 | 320 | 65.5 | 73.6 | 48.2 |

Table 2-continued

| Example No. | Catalyst Composition (Atomic ratios of elements other than oxygen) | | | | | | | NT (°C.) | Conversion of methacrolein (mol %) | Selectivity for methacrylic acid (mol %) | Per-pass yield of methacrylic acid (mol %) |
|---|---|---|---|---|---|---|---|---|---|---|---|
| | P | V | Na | K | Rb | Cs | Mo | | | | |
| 32 | 1 | 2 | — | 1.0 | — | — | 12 | 290 | 75.5 | 70.1 | 52.9 |
| 33 | 1 | 3 | — | 1.0 | — | — | 12 | 310 | 73.0 | 65.0 | 47.4 |
| 34 | 2 | 1 | — | 1.0 | — | — | 12 | 285 | 79.6 | 75.6 | 60.2 |
| 35 | 3 | 1 | — | 1.0 | — | — | 12 | 300 | 74.3 | 76.0 | 56.5 |
| 36 | 4 | 1 | — | 1.0 | — | — | 12 | 310 | 64.4 | 72.1 | 46.4 |
| 37 | 1 | 1 | 1.0 | — | — | — | 12 | 300 | 70.4 | 68.2 | 48.0 |
| 38 | 1 | 1 | — | — | 1.0 | — | 12 | 300 | 77.3 | 70.6 | 54.6 |
| 39 | 1 | 1 | — | — | — | 1.0 | 12 | 280 | 81.4 | 74.7 | 60.8 |

Control 1

106 grams of ammonium molybdate was dissolved in 400 ml of hot water. Separately, 9.8 grams of oxalic acid was dissolved in 100 ml of water, after which 4.6 grams of vanadium pentoxide was added with heating followed by well stirring the mixture until a deep blue homogeneous solution was obtained. This latter solution was then added to the foregoing aqueous ammonium molybdate solution, after which the resulting combined solution was evaporated to dryness with stirring. The resulting solid was then dried for 4 hours at 200° C., comminuted to a particle size of about 5 mm, and thereafter calcined for 5 hours at 400° C. under circulation of air. The composition of the so obtained catalyst, when expressed in atomic ratios exclusive of oxygen, was $V_1Mo_{12}$. This catalyst was used for oxidizing methacrolein with the results shown in Table 3.

Control 2

A catalyst of the composition shown in Table 3 was prepared by operating as in Example 1 but without adding copper nitrate and potassium hydroxide in preparing the catalyst. This catalyst was used in oxidizing methacrolein with the results shown in Table 3.

Control 3

A catalyst having the composition shown in Table 3 was prepared by operating exactly as in Example 27 but without using vanadium pentoxide and oxalic acid. This catalyst was used in oxidizing methacrolein with the results shown in Table 3.

Control 4

A catalyst having the composition shown in Table 3 was prepared by operating exactly as in Example 27 but without using orthophosphoric acid. This catalyst was used in oxidizing methacrolein with the results shown in Table 3.

Control 5

22.2 grams of ammonium metavanadate and 106 grams of ammonium molybdate were dissolved in 400 ml of hot water. After adding 7.3 grams of antimony trioxide to the resulting solution, it was evaporated to dryness with stirring. After drying the resulting solid for a further 4 hours at 200° C., it was comminuted into a particle size of about 5 mm and thereafter calcined for 5 hours at 400° C. under circulation of air to obtain a catalyst having the composition shown in Table 3. This catalyst was used, and the oxidation of methacrolein was carried out with the results shown in Table 3.

Control 6

106 grams of ammonium molybdate was dissolved in 400 ml of hot water, after which 11.6 grams of 85% orthophosphoric acid was admixed therewith followed by the addition also of 14.6 grams of antimony trioxide. This mixture was then evaporated to dryness with stirring. The resulting solid was dried for a further 4 hours at 200° C. and thereafter comminuted to a particle size of about 5 mm followed by calcination for 5 hours at 400° C. under circulation of air to obtain a catalyst of the composition shown in Table 3. This catalyst was used in oxidizing methacrolein with the results shown in Table 3.

Control 7

In preparing the catalyst as in Control 5, 530 grams of an aluminum sponge of 6–10-mesh size produced by Mitsuwa Chemical Co., Ltd. Japan, was added as carrier material subsequent to the addition of the antimony trioxide, following which the mixture was evaporated to dryness. Thereafter, the experiment was operated as in Control 5 to prepare the catalyst, which was then used in oxidizing methacrolein. The results obtained are shown in Table 3.

Table 3

| Control No. | Catalyst Composition (Atomic ratios of elements other than oxygen) | | | | | Reaction Conditions | | Conversion of methacrolein (mol %) | Selectivity for methacrylic acid (mol %) | Per-pass yield of methacrylic acid (mol %) |
|---|---|---|---|---|---|---|---|---|---|---|
| | Y | X | P | V | Mo | Space velocity (hr$^{-1}$) | NT (°C.) | | | |
| 1 | 0 | 0 | 0 | 1 | 12 | 1000 | 280 | 56.7 | 20.3 | 11.5 |
| 2 | 0 | 0 (K) | 2 | 1 | 12 | 1000 | 315 | 62.8 | 55.9 | 35.1 |
| 3 | 0 | 1 (K) | 1 | 0 | 12 | 1000 | 280 | 47.0 | 44.4 | 20.9 |
| 4 | 0 (Sb) | 1 | 0 | 1 | 12 | 1000 | 330 | 41.5 | 32.5 | 13.5 |
| 5 | 1 (Sb) | 0 | 0 | 3.8 | 12 | 1000 | 320 | 72.3 | 16.5 | 11.5 |
| 6 | 2 | 0 | 2 | 0 | 12 | 1000 | 305 | 29.7 | 57.7 | 17.0 |

Table 3-continued

| Control No. | Catalyst Composition (Atomic ratios of elements other than oxygen) | | | | | Reaction Conditions | | Conversion of methacrolein (mol %) | Selectivity for methacrylic acid (mol %) | Per-pass yield of methacrylic acid (mol %) |
|---|---|---|---|---|---|---|---|---|---|---|
| | Y | X | P | V | Mo | Space velocity (hr$^{-1}$) | NT (°C.) | | | |
| 7 | (Sb) 1 | 0 | 0 | 3.8 | 12 | 1000 | 320 | 34.5 | 21.1 | 7.3 |

We claim:

1. A process for preparing methacrylic acid which comprises carrying out the catalytic vapor phase oxidation of methacrolein with a molecular oxygen-containing gas in the presence of a catalytic oxide consisting essentially of molybdenum, vanadium, phosphorus, at least one metallic element Y selected from the group consisting of copper, cobalt, zirconium, bismuth, antimony and aresenic, and at least one alkali metal element selected from the group consisting of sodium, potassium, rubidium and cesium, at an atomic ratio of molybdenum to vanadium to phosphorus to the metallic element Y to the alkali metal element to oxygen of 12:0.1-10:0.1-10:a:b:f, wherein "a" is a positive number up to and including 10, "b" is a positive number up to and including 10 and "f" is a value that is determined by the valences and atomic ratios of the other elements present, wherein the vanadium component of said catalytic oxide is in the form of a complex prepared by reacting vanadium pentoxide and orthophosphoric acid.

2. The process of claim 1 which comprises carrying out the catalytic vapor phase oxidation reaction at a temperature of 200°–400° C., a pressure of normal atmospheric pressure-10 atmospheres, and a space velocity of 500–3000 hr$^{-1}$.

3. The process of claim 1 which comprises carrying out the catalytic vapor phase oxidation at a temperature of 230°–350° C., a pressure of normal atmospheric pressure to 10 atmospheres, and a space velocity of 500–3,000 hr$^{-1}$, and wherein the atomic ratio of molybdenum to vanadium to phosphorus to Y to alkali metal element to oxygen is 12:0.5-5.0:0.5-5.0:a:b:f, wherein "a" is a positive number up to and including 8.0 and "b" is a positive number up to and including 3.0, and "f" is a value that is determined by the valences and atomic ratios of the other elements present.

4. The process of claim 3 wherein "b" is a positive number of from 0.5 to 2.0.

5. The process of claim 1 wherein said metallic element Y is cobalt.

6. The process of claim 1 wherein said metallic element Y is zirconium.

7. The process of claim 1 wherein said metallic element Y is antimony.

8. The process of claim 1 wherein said alkali metal element is sodium.

* * * * *

UNITED STATES PATENT AND TRADEMARK OFFICE
CERTIFICATE OF CORRECTION

PATENT NO. : 4,180,678
DATED : December 25, 1979
INVENTOR(S) : WADA, ET AL.

It is certified that error appears in the above-identified patent and that said Letters Patent are hereby corrected as shown below:

Please add the following priority data to item [30] on page 1
-- January 19, 1974 [JP] Japan............49-8233 --

Signed and Sealed this

Eleventh Day of March 1980

[SEAL]

Attest:

SIDNEY A. DIAMOND

Attesting Officer    Commissioner of Patents and Trademarks